(12) United States Patent
Wei et al.

(10) Patent No.: US 9,789,032 B2
(45) Date of Patent: Oct. 17, 2017

(54) COLOR COSMETIC WITH HIGH COVERAGE AND NATURALNESS

(75) Inventors: Xiaolan Wei, Suffern, NY (US); Prithwiraj Maitra, Randolph, NJ (US)

(73) Assignee: AVON PRODUCTS, INC., Rye, NY (US)

( * ) Notice: Subject to any disclaimer, the term of this patent is extended or adjusted under 35 U.S.C. 154(b) by 354 days.

(21) Appl. No.: 13/497,439

(22) PCT Filed: Dec. 21, 2010

(86) PCT No.: PCT/US2010/061459
§ 371 (c)(1),
(2), (4) Date: Mar. 21, 2012

(87) PCT Pub. No.: WO2011/082019
PCT Pub. Date: Jul. 7, 2011

(65) Prior Publication Data
US 2012/0276031 A1    Nov. 1, 2012

Related U.S. Application Data

(60) Provisional application No. 61/291,174, filed on Dec. 30, 2009.

(51) Int. Cl.
| | |
|---|---|
| *A61K 8/891* | (2006.01) |
| *A61Q 1/02* | (2006.01) |
| *A61K 8/02* | (2006.01) |
| *A61K 8/19* | (2006.01) |
| *A61K 8/26* | (2006.01) |
| *A61K 8/29* | (2006.01) |
| *A61K 8/58* | (2006.01) |
| *A61K 8/895* | (2006.01) |
| *A61Q 1/04* | (2006.01) |
| *A61Q 1/06* | (2006.01) |
| *A61Q 1/08* | (2006.01) |
| *A61Q 1/10* | (2006.01) |
| *A61Q 1/12* | (2006.01) |

(52) U.S. Cl.
CPC ............ *A61K 8/025* (2013.01); *A61K 8/0245* (2013.01); *A61K 8/0254* (2013.01); *A61K 8/19* (2013.01); *A61K 8/26* (2013.01); *A61K 8/29* (2013.01); *A61K 8/585* (2013.01); *A61K 8/891* (2013.01); *A61K 8/895* (2013.01); *A61Q 1/02* (2013.01); *A61K 2800/612* (2013.01); *A61K 2800/614* (2013.01); *A61Q 1/04* (2013.01); *A61Q 1/06* (2013.01); *A61Q 1/08* (2013.01); *A61Q 1/10* (2013.01); *A61Q 1/12* (2013.01)

(58) Field of Classification Search
USPC ......................................................... 424/63
See application file for complete search history.

(56) References Cited

U.S. PATENT DOCUMENTS

| | | |
|---|---|---|
| 3,373,134 A | 3/1968 | Yasui et al. |
| 4,124,688 A | 11/1978 | Shibazaki et al. |
| 4,159,312 A | 6/1979 | Shibazaki et al. |
| 4,781,917 A | 11/1988 | Luebbe et al. |
| 5,688,831 A | 11/1997 | El-Nokaly et al. |
| 6,488,756 B1 | 12/2002 | Schoen et al. |
| 6,531,540 B1 | 3/2003 | O'Brien |
| 7,241,835 B2 | 7/2007 | O'Brien et al. |
| 7,780,971 B2 | 8/2010 | Chevalier et al. |
| 2002/0192250 A1 | 12/2002 | Chevalier et al. |
| 2003/0003064 A1 * | 1/2003 | Kalla et al. ............... 424/63 |
| 2005/0112154 A1 | 5/2005 | Giroud et al. |
| 2007/0020208 A1 | 1/2007 | Gutkowski et al. |
| 2009/0081316 A1 | 3/2009 | Wahl et al. |

FOREIGN PATENT DOCUMENTS

| | | | |
|---|---|---|---|
| EP | 1136064 A2 * | 9/2001 | ............ A61K 7/48 |
| EP | 1291370 A1 | 3/2003 | |
| JP | S61194010 A | 8/1986 | |
| JP | H05221634 A | 8/1993 | |
| JP | 07196316 A * | 8/1995 | ............ C01F 11/18 |
| JP | 2006062995 A | 3/2006 | |
| JP | 2007084478 A | 4/2007 | |
| JP | 2008088317 A | 4/2008 | |
| WO | 02/056846 A1 | 7/2002 | |
| WO | 03/080005 A1 | 10/2003 | |
| WO | 2004/045524 A2 | 6/2004 | |

OTHER PUBLICATIONS

Anon. Anon. "Velvesil FX gel-powder", IP.com Journal. 2008. vol. 8.*
Yun Shao. "Pigment Surface Treatment". Kobo Products. Technical Seminar. Apr. 14, 2008).*
Velvesil FX gel-powder, Datasheet [online], Momentive Performance Materials, Mar. 2008 [retrieved on Jan. 30, 2011 from the internet http:\www.momentive.com/momentiveInternetDoc/MPM/Static%20Fukes/Documents/Data% 20Sheets/Velvesil_FX_MD.indd.pdf p. 2, 8, 12, 15.
Shao "Pigment Surface Treatment" Kobo Products, Technical Seminar; published on Apr. 14, 2008.
Anonymous: "Adina Cosmetic Ingredients", Internet Citation, Nov. 1, 2006, pp. 1-4 URL:http://www.cosmeticingredients.co.uk/adinaformulate06.pdf.

* cited by examiner

*Primary Examiner* — David J Blanchard
*Assistant Examiner* — Nicole Babson
(74) *Attorney, Agent, or Firm* — Brian McCloskey; Elizabeth Morters

(57) ABSTRACT

Described herein is a cosmetic composition comprising a mixture of metal oxide pigments having different shapes and sizes which provides high coverage and a natural look upon application.

17 Claims, 3 Drawing Sheets

COLOR COSMETIC WITH HIGH COVERAGE AND NATURALNESS

CROSS REFERENCE TO RELATED APPLICATIONS

This application claims priority to International Application Serial No. PCT/US10/61459 filed Dec. 21, 2010, which claims priority U.S. Provisional Patent Application Ser. No. 61/291,174 filed Dec. 30, 2009, the contents of which are hereby incorporated by reference in their entirety.

FIELD OF INVENTION

The present invention relates generally to color cosmetics, and in particular to color cosmetics, such as foundations, that simultaneously provide high coverage with a natural look. The color cosmetic compositions according to the invention comprise pigments having two or more distinct morphologies.

BACKGROUND

Makeup used to create the appearance of an even skin tone, which is affected by the optical geometry of the makeup and/or particles comprised in the makeup. When light is aimed in the direction of an object, the light may be directed as a reflection completely in one direction determined by the angle of incidence (e.g., similar to the well-known reflection phenomenon seen with a mirror). Light may also scatter in many different directions in a manner referred to as diffuse transmittance. Furthermore, the light may transmit through the makeup, if the makeup possesses sufficient transparency. This phenomenon also involves the refraction of light. As the light passes through the object its speed (or velocity) and wavelength changes according to the index of refraction, defined by the ratio of the speed of light in vacuum to the speed of light in the object. The light bends as it passes through the object.

When the surface of the skin is smooth, light is absorbed, reflected and scattered off the skin and is observed as a color according to how much light is absorbed and scattered. Blemishes on the skin absorb, reflect, and scatter light to varying degrees, and thus, prevent the appearance of a flawless complexion. Furthermore, when light is directed toward a wrinkle, it is unable to be reflected or even scattered and the eye observes a darkness where the line or wrinkle is located on the skin.

Additionally, the angle at which make up worn by a person will affect visual impression received by the observer, such looking straight at the person (zero viewing angle) will appear different to the observer than other portions of the made up anatomy seen at a different angle.

Light manipulation, therefore, has become an important development in makeup used to create the appearance of an even skin tone.

Current makeup systems generally comprise traditionally high refractive pigments (e.g., titanium dioxide ($TiO_2$) and iron oxide colorants) which manipulate the light, and modify the appearance of the surface to which it is applied. However, this method has been found to be undesirable because it is too opaque and reflective, i.e., due to the isotropic back scattering properties of $TiO_2$, a high concentration of $TiO_2$ provides high coverage at the expense of a natural look. In contrast, a low concentration of $TiO_2$ achieves a cosmetic film that looks more natural (e.g., not chalky) at the expense of sufficient coverage. Therefore, it has been suggested that pigment not only diffuse light but also have a certain amount of reflectance to overcome the mask-like appearance of titanium dioxide. While it is always desirable to have an optimal combination of naturalness and coverage, it is not readily achievable because of the isotropic nature of the traditional pigments.

Generally, diffusion or blurring may be achieved with spherical soft focus particles such as nylon and polyurethane particles and/or interference pigments. However, although anisotropic pigments have been designed, there is an ongoing need for makeup compositions to provide sufficient coverage, e.g., to create the appearance of an even skin tone, and achieve a natural look upon application.

SUMMARY OF INVENTION

The present invention is founded on the discovery that a cosmetic composition comprising a mixture of metal oxide particles (e.g., titanium dioxide) of various sizes and shapes may simultaneously provide high coverage on the skin and achieve a natural look characterized by high diffuse transmittance.

In one aspect of the invention, cosmetic compositions are provided comprising: (i) a first pigment component comprising metal oxide particles bonded to an alumina platelet, and (ii) a second pigment component comprising metal oxide particles. The cosmetic compositions of the invention may further optionally contain (iii) calcium carbonate powder having a cubic crystalline form and an average particle size typically between about 0.1 and about 20 microns. The weight ratio of said first pigment to said second pigment is typically 1:5 to 5:1, and, when present, to said calcium carbonate is typically from about 1-5:1-5:1-5.

The first pigment component may, for example, comprise titanium dioxide particles bonded to an alumina platelet and the second pigment component may comprise titanium dioxide particles, which themselves may be substantially spherical. In another embodiment the titanium dioxide particles are bonded to a spherical polymethyl methacrylate substrate. The benefits of the invention may be more fully realized when the cosmetic composition further comprises a silicone-based crosslinked elastomeric gelling agent, and most fully realized when the cosmetic composition additionally comprises both the silicone-based crosslinked elastomeric gelling agent including boron nitride particulates for providing an additional soft-focus effect. The compositions may include additional colorants, such as pearls and pigments, and in particular, iron oxide pigments.

A cosmetic composition as described herein may be used for any cosmetic that aims to provide sufficient coverage and achieve a natural look upon application. Such a cosmetic may be, but is not limited to, a foundation (e.g., liquid foundation, foundation mousse, foundation stick, compact foundation, loose powders, compact powders, etc.), an eye shadow, a lipstick, a nail enamel, a hair care product, a skin care product, and a personal care product.

In another aspect of the invention there is provided a method of improving the uniformity of a cosmetic applied on a skin surface as viewed by an observer of the cosmetic on said skin surface, at different angles, comprising topically applying to the skin surface a composition according to the invention.

DETAILED DESCRIPTION

Figure 1:
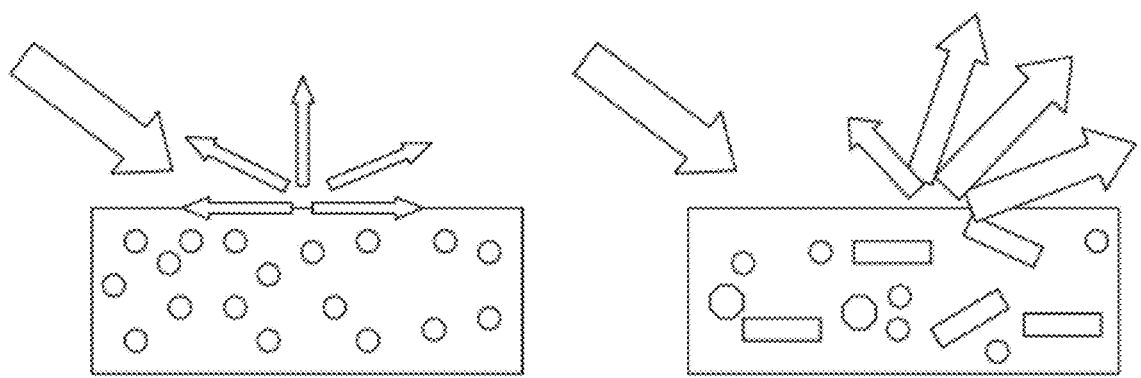
FIG. 1 is a schematic representation of the light-bending effect of traditional high refractive pigments and a mixture of metal oxide particles of various sizes and shapes.

A drawback to conventional color cosmetics is the isotropic light scattering that results from the pigments employed. The effect is an unnatural appearance compared to the anisotropic light scattering properties of human skin. This phenomenon is schematically depicted in FIG. 1. While some soft focus material are known which produce a more natural look, these materials often suffer the disadvantage of providing inadequate coverage on the skin. Additionally, the angle at which make up worn by a person will affect visual impression received by the observer, such looking straight at the person (zero viewing angle) will appear different to the observer than other portions of the made up skin surface seen at a different angles, thereby providing superior uniformity of the cosmetic on the skin of the wearer, as observed by another.

It has surprisingly been discovered that a more natural appearance is possible in a color cosmetic, such as a foundation, through the use of a particular combination of pigments having distinct morphologies. The cosmetic compositions according to the invention comprise (i) a first pigment component comprising a colorant bonded to a platelet-shaped substrate, and (ii) a second pigment component comprising metal oxide pigment particles, the compositions providing anisotropic light scattering properties similar to that of human skin, while at the same time providing a high level of coverage on the skin. The cosmetic compositions of the invention may further optionally contain (iii) calcium carbonate powder having a cubic crystalline form and an average particle size between about 0.1 and about 20 microns as used herein, "consisting essentially of" means that the composition or component may include additional ingredients, but only if the additional ingredients do not materially alter the basic and novel characteristics of the claimed compositions or methods. All percent are by weight of the total composition, unless otherwise indicated.

The first pigment component of the invention is a particulate colorant which comprises (i) a particulate modifying agent; and (ii) a first colorant bonded to the surface of the particulate modifying agent. As used herein, the term "colorant" generally refers to a color extender, dye, pigment, lake, toner, other agent, or a combination thereof, used to impart a color to a material, and includes inorganic, organic, water-soluble and water-insoluble substances. As used herein, the term "modifying agent" includes a substrate responsible for imparting additional optical or visual properties to the material.

The particulate colorant may be formed according to the procedures described in SENSIENT COLORS INC.'S U.S. Patent Pub. 2007/0020208, the disclosure of which is hereby incorporated by reference herein. For example, the particulate colorant may be prepared by blending, either in dry form or as slurries or solutions, the first colorant with the particulate modifying agent. The first colorant may be bonded to the surface of the particulate modifying agent by, for example, adding a surface treatment to the dry blend. By "bonded" is meant chemical bonding through strong interactions, for example, ionic or covalent bonds, or by physical bonding through weak interactions, for example, by dipole-dipole interactions such as hydrogen bonds, charge-transfer complexes, hydrophobic interactions, van der Waals forces, or combinations thereof.

The modifying agent may be, without limitation, a metal oxide, such as aluminum oxide (alumina), zinc oxide, silicon dioxide (silica), magnesia, or a combination thereof; talc; mica; kaolin; bismuth oxychloride; stainless steel; graphite; or platy metals such as bronze, copper and aluminum or a combination thereof. A preferred modifying agent comprises a metal oxide; in particular alumina. The modifying agent may be in the shape of a platelet, for example, a platelet of alumina. As used herein, the term "platelet" generally refers to a substantially planar and flaky material that is generally not spherical and is greater in width and length than in thickness. For example, suitable platelets may have an average diameter of between 1 and 20 microns, and an average thickness less than 0.5 microns. In some embodiments, the edge of the platelet is substantially free of colorant, by which is meant that at least 90% of the total surface area of the edge of the modifying agent has no colorant adhered or bonded to it. The top and bottom faces of the platelet will typically have the first colorant adhered to about 5% to about 90% of their surface area. In some embodiments, the first colorant may cover or coat more than about 1%, 3%, 5%, 10%, 15%, 20%, 30%, 40% or 50% of the total surface area of the modifying agent and less than about 99%, 95%, 90%, 85%, 80%, 75%, 65%, 50%, 40%, 30%, 25%, 20%, 15% or 10%, of the total surface area of the modifying agent. According to SENSIENT COLORS INC.'S U.S. Patent Pub. 2007/0020208, these particulate colorants may exhibit increased burnishing when compared with platelet alumina completely coated with colorant.

The first colorant may comprise, for example, an inorganic pigment. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, y-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Non-metal oxides such as alumina and silica, ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like, are also contemplated to be suitable inorganic pigments.

The first colorant may comprise, for example, an organic pigment. Organic pigments can include, but are not limited to, at least one of carbon black, carmine, phthalocyanine blue and green pigment, diarylide yellow and orange pigments, and azo-type red and yellow pigments such as toluidine red, litho red, naphthol red and brown pigments, and combinations thereof.

The first colorant component may comprise, for example, one or more dyes, toners or lakes. Lakes generally refer to a colorant prepared from a water-soluble organic dye (e.g., D&C or FD&C) which has been precipitated onto an insoluble reactive or adsorptive substratum or diluent. The term "D&C" means drug and cosmetic colorants that are approved for use in drugs and cosmetics by the FDA. The term "FD&C" means food, drug, and cosmetic colorants which are approved for use in foods, drugs, and cosmetics by the FDA. Certified D&C and FD&C colorants are listed in 21 C.F.R. §74.101 et seq. and include the FD&C colors Blue 1, Blue 2, Green 3, Orange B, Citrus Red 2, Red 3, Red 4, Red 40, Yellow 5, Yellow 6, Blue 1, Blue 2; Orange B, Citrus Red 2; and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on.

Substrates suitable for forming lakes include, without limitation, mica, bismuth oxychloride, sericite, alumina, aluminum, copper, bronze, silver, calcium, zirconium, barium, and strontium, titanated mica, fumed silica, spherical silica, polymethylmethacrylate (PMMA), micronized TEFLON, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, nylon, silica silylate, silk powder, sericite, soy flour, tin oxide, titanium hydroxide, trimagnesium phosphate, walnut shell powder, and mixtures thereof.

Suitable lakes include, without limitation, those of red dyes from the monoazo, disazo, fluoran, xanthene, or indigoid families, such as Red 4, 6, 7, 17, 21, 22, 27, 28, 30, 31, 33, 34, 36, and Red 40; lakes of yellow pyrazole, monoazo, fluoran, xanthene, quinoline, dyes or salt thereof, such as Yellow 5, 6, 7, 8, 10, and 11; lakes of violet dyes including those from the anthroquinone family, such as Violet 2. as well as lakes of orange dyes, including Orange 4, 5, 10, 11, and the like. Suitable Lakes of D&C and FD&C dyes are defined in 21 C.F.R. §82.51.

The first colorant component may have any shape, including without limitation, spherical, cubic, acicular, and platelet-shaped. In one embodiment, the first colorant component is titanium dioxide having a substantially spherical shape.

The surface treatment may be any such treatment that modifies the surface of the modifying agent and/or the first colorant. For example, the surface treatment may make the particles more hydrophobic or more dispersible in a vehicle or may increase the adhesion of the first colorant to the modifying agent. The surface of the particles may, for example, be covalently or ionically bound to an organic molecule or silicon-based molecule or may be adsorbed thereto, or the particle may be physically coated with a layer of material. The surface treatment compound may be attached to the particle through any suitable coupling agent, linker group, or functional group (e.g., silane, ester, ether, etc). The compound may comprise a hydrophobic portion which may be selected from, for example, alkyl, aryl, allyl, vinyl, alkyl-aryl, aryl-alkyl, organosilicone, di-organosilicone, dimethicones, methicones, polyurethanes, silicone-polyurethanes, and fluoro- or perfluoro-derivatives thereof. Other hydrophobic modifiers include lauroyl lysine, Isopropyl Titanium Triisostearate (ITT), ITT and Dimethicone (ITT/Dimethicone) cross-polymers, ITT and Amino Acid, ITT/Triethoxycaprylylsilane Crosspolymer, waxes (e.g., carnauba), fatty acids (e.g., stearates), HDI/Trimethylol Hexylactone Crosspolymer, PEG-8 Methyl Ether Triethoxysilane, aloe, jojoba ester, lecithin, Perfluoroalcohol Phosphate, and Magnesium Myristate (MM), to name a few.

The surface treatment may comprise, in some embodiments, a material selected from aluminum laurate, aluminum stearate, an amino acid, chitin, collagen, fluorochemical, lecithin, metal soap, natural wax, polyacrylate, polyethylene, silicone, silane, titanatate ester, urethane, dimethicone, perfluoropolymethylisopropyl ether, styrene acrylates copolymer, magnesium myristate, lauroyl lysine and a combination thereof. In other embodiments, the surface treatment comprises a material selected from methicone, triethoxycaprylylsilane, trimethoxycaprylylsilane, dimethicone copolyol and a combination thereof.

In one embodiment, the particulate colorant has been surface treated with an alkylsilane, such as a $C_{1-20}$ alkylsilane, or more typically a $C_{1-12}$ alkylsilane, including an exemplary embodiment wherein the particle is surface-treated with a $C_8$ alkylsilane (e.g., caprylylsilane). The colorants may be prepared, for example, by treating a particulate with a trialkoxyalkylsilane, such as Triethoxycaprylylsilane (INCI).

In another embodiment, the particulate colorant has been surface treated with a fluoroalkylsilane, and in particular a perfluoroalkylsilane, such as a $C_{1-20}$ perfluoroalkylsilane, or more typically a $C_{1-12}$ perfluoroalkylsilane, including an exemplary embodiment wherein the particulate colorant is surface-treated with a $C_8$ perfluoroalkylsilane. These may be prepared by treating a particulate colorant with a trialkoxyfluoroalkylsilane, such as Perfluorooctyl Triethoxysilane (INCI). An example of such a compound is tridecafluorooctyltriethoxy silane, available from Sivento, Piscataway, N.J., under the trade name DYNASILANE™ F 8261.

In some embodiments, the alkyl silane surface-treated colorant consists essentially of or comprises an alumina substrate (e.g., platelet shaped) and a pigment, dye, or lake bonded to the alumina substrate by an alkyl silane surface treatment. Typically, the alkyl silane will be octylsilane and may be formed by treatment with Triethoxycaprylylsilane. Nonlimiting examples of such colorants include, but are not limited to, Alumina/Titanium Dioxide/Triethoxycaprylylsilane 1% (COVALUMINE™ Atlas White AS), Alumina/D&C Red Aluminum Lake CTD/Triethoxycaprylylsilane 1% (COVALUMINE™ Red Rose AS), Alumina/D&C Red Aluminum Lake CTD/Triethoxycaprylylsilane 1% (COVALUMINE™ Sonoma Red AS), Alumina/Black Iron Oxide CTD/Triethoxycaprylylsilane 1% (COVALUMINE™ Sonoma Black AS), Alumina/D&C Red #6 Aluminum Lake CTD/Triethoxycaprylylsilane 1% (COVALUMINE™ Fire Red AS), Alumina/Yellow Iron Oxide CTD/Triethoxycaprylylsilane 1% (COVALUMINE™ Sonoma Yellow AS), Alumina/D&C Blue #1 Aluminum Lake CTD/Triethoxycaprylylsilane 1% (COVALUMINE™ Astral Blue AS), Alumina/Carmine CTD/Triethoxycaprylylsilane 1% (COVALUMINE™ Campari AS), Alumina/Yellow #5 CTD/Triethoxycaprylylsilane 1% (COVALUMINE™ Sunburst AS), Alumina/Triethoxycaprylylsilane 1%, and combinations thereof, each of which is available from SENSIENT™ Cosmetic Technologies LCW.

The first pigment component may comprise a total of about 0.1% to about 75% by weight of the composition, based on the total weight of the composition, more typically from about 0.5% to about 25% by weight, and preferable from about 1% to about 10% by weight of the total composition.

In a preferred embodiment, the first pigment component comprises spherical titanium dioxide particles bonded to an alumina platelet with a Triethoxycaprylylsilane surface coating comprising about 1% by weight of the pigment. Such a pigment has the INCI name Alumina/Titanium Dioxide/Triethoxycaprylylsilane 1% and is commercially available from SENSIENT TECHNOLOGIES under the tradename COVALUMINE™ Atlas White AS.

The second pigment component is a metal oxide, especially titanium dioxide, having a geometry that is different than the platelet geometry of the first pigment component, for example, a spherical, acicular, cubic, etc. geometry. In a preferred embodiment the geometry of the second pigment component is spherical. The second pigment component may also comprise a surface treatment, which may be any of the surface treatments disclosed above. The amount of surface treatment may range from about 0.5% to about 5% by weight, but will more typically be in the range of about 1% to about 3% by weight.

The second pigment component may comprise a total of about 0.1% to about 75% by weight of the composition, based on the total weight of the composition, more typically from about 0.5% to about 25% by weight, and preferable from about 1% to about 10% by weight of the total composition. The weight ratio of the first pigment component to the second pigment may be 1:5 to 5:1; 1:2.5 to 2.5:1; 1:1.25 to 1.25:1, and 1:1.

In one aspect of the invention, the second pigment component according the invention comprises a substantially spherical porous microsphere of polymethyl methacrylate (PMMA) polymer substrate having a colorant bonded to the surface thereof. The colorant may be any colorants described above in connection with the first pigment component and may be, for example, spherical, platelet-shaped, acicular, cubic, etc. Preferred colorants include metal oxide pigments such as titanium dioxide and iron oxides. In this embodiment the second pigment component may also comprises a surface treatment, which may be any of the surface treatments disclosed above, in the amount of from about 0.5% to about 5% by weight, but will more typically be in the range of about 1% to about 3% by weight. The weight ratio of pigment to PMMA polymer may range from about 1:2 to about 2:1, or from about 2:3 to about 3:2, and is preferably about 1:1.

In another embodiment, the second pigment component comprises spherical titanium dioxide particles bonded to the surface of a porous PMMA particle and further comprising a Triethoxycaprylylsilane surface-treatment. In one embodiment, the porous microspheres of Polymethyl Methacrylate comprise about 49% by weight of the second pigment, the titanium dioxide comprises about 48.5% by weight of the second pigment, and the Triethoxycaprylylsilane surface treatment comprises about 2.5% by weight of the second pigment.

The cosmetic composition of the invention may optionally comprise a third particulate component, which is a calcium carbonate powder having a cubic crystalline morphology. Suitable cubic calcium carbonate powders are described in U.S. Pat. No. 4,124,688 and U.S. Pat. No. 4,159,312, the disclosures of which are hereby incorporated by reference. The cubic calcium carbonate powders are preferably precipitated calcium carbonate powders. One such calcium carbonate is available from SPECIALTY MINERALS under the tradename HEAVY PCC. The average particle size of the calcium carbonate may be, for example, from about 0.1 microns to about 30 microns, but will more typically range from about 0.5 microns to about 30 microns, or from about 1 micron to about 15 microns.

The third component may comprise a total of about 0.1% to about 35% by weight of the composition, based on the total weight of the composition, more typically from about 0.5% to about 15% by weight, and preferable from about 1% to about 10% by weight of the total composition.

The relative weight ratios of the first pigment, the second pigment, and the cubic calcium carbonate will typically be within the range of about 1-10:1-10:1-10, more typically about 1-5:1-5:1-5, or about 1-2:1-2:1-2. The inventive combination will typically comprise from about 1% to about 100% by weight of a cosmetic composition, and more often will comprise from about 1% to about 75% by weight of such a composition. In some preferred embodiments, the combination will comprise from about 5% to about 25% by weight of the composition.

The compositions may include a suitable film formers, including, but not limited to, sulfopolyester resins, polyvinylacetate, polyvinyl alcohol polymers, acrylic resins, polyvinylpyrrolidones, high molecular weight silicones, organosiloxanes, polyurethanes, hydrophobic acrylate copolymers, silicone acrylate polymers (including those available from SHIN ETSU as KP-549, KP-550, X-22-8247, X-22-8278, X-22-8299, KP-561, KP-562P, KP 573, and X-52-2432B; and those available from DOW CORNING as FA 4001 CM and FA4002 ID), silicone cross-polymers, as well as others known in the art (for example those listed in WO 03/105790, incorporated by reference herein). The film former is preferably present from about 0.01. weight % to about 20 weight % of the total weight of the composition.

In some embodiments, the naturalness and coverage of the inventive pigment combination, in particular the uniformity of the coverage of the wearer of the cosmetic as viewed by an observer, especially as viewed at different viewing angles, is enhanced by incorporating the pigments into a vehicle which comprises a silicone cross polymer (i.e., elastomer) gelling agent.

Suitable silicone elastomers are obtained by crosslinking reaction among multiple silicone backbone units. In one embodiment, silicone elastomers are obtained by a crosslinking addition reaction of a diorganosiloxane comprising at least one hydrogen bonded to silicon and a crosslinker with two ethylenically unsaturated groups. The silicone backbone can contain additional functional groups, either on the pendant or terminal positions. Examples of the functional groups include, but are not limited to, alkyl groups comprising from 1 to 100 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. The crosslinker can also have functional groups between the ethylenically unsaturated groups. Examples of such functional groups include, but are not limited to, alkyl groups comprising from 1 to 100 carbon atoms, such as methyl, ethyl, propyl, butyl, octyl, decyl, dodecyl (or lauryl), myristyl, cetyl or stearyl; polyether including PEO ($-CH_2-O-CH_2-O-$), PPO ($-CH_2-CH(CH_3)-O-$), and a combination thereof, and polyglycerolate. The silicone elastomers can also be cross-linked via functional groups that are attached to the silicone backbone. The functional groups can be attached at the pendant or terminal positions. Examples include polymerization of functionalities via acrylate or epoxide.

The silicone elastomers can be used as pure materials or as elastomers swelled in a suitable solvent. Examples of solvent include silicone diluents or dispersants including but not limited to cyclomethicone, dimethicone, diethicone, caprylyl methicone, methyltrimethicone, organic diluents including isohexadecane, isododecane, squalane, and triethylhexanoin. The silicone elastomers can further contain particles in their network, for example the crosslinked elastomer can include boron nitride, nylon, polyurethane, and combinations thereof.

Suitable crosslinked silicone polymers include: KSG-6, KSG-15, KSG-16, KSG-18, KSG-21, KSG-20, KSG-30, KSG-31, KSG-32, KSG-33, KSG-41, KSG42, KSG-43, KSG-44, KSG-210, KSG-310, KSG-320, KSG-330, KSG-340, KSG-360Z, KSG-710, KSG-810, KSG-820, KSG-830, KSG-840, USG-105, USG-106 and USG-107, and X-22-6146 from SHIN-ETSU; DC9010 and DC9011, DC9040, DC9041, DC9043, DC9045, DC9350, DC9509, DC9505, DC9506, and DC9530 from DOW CORNING; GRANSIL CD-10, DMG-2, GCM-5, GTS, GVL, IDS-5, MLB, PC-12, RPS, DM-5, DM-5LV, DMCM-5, DMDM-25, DMID, DMVR, GAM, and GVR from GRANT INDUSTRIES, and SFE 839, VELVESIL 125, VELVESIL DM, VELVESIL FX gel powder, and VELVESIL 034 by MOMENTIVE PERFORMANCE MATERIALS, and combinations thereof.

In one embodiment the elastomeric gelling agent has a silicone backbone crosslinked with a cyclic epoxide, especially an alkyl cylcohexylepoxide, which may further contain boron nitride, and optionally alkyl-methicone (e.g., Caprylyl Methicone) dispersant/spreading aid. The boron nitride will typically have a particle size in the range of about 1 micron to about 30 microns, but will more typically be within the range of about 6 micron to about 15 microns. An average particle size of about 11 microns offers a good balance between soft focus and coverage. The gelling agent is preferably a silicone cross-polymer gelling agent and may include, without limitation, those described in U.S. Pat. Nos. 6,444,745, 6,531,540, 6,538,061, 6,759,479, and 7,241,835, the disclosures of which are hereby incorporated by reference in their entirety. This crosslinked gelling agent is sold under the trade name VELVESIL DM, VELVESIL 034, and VELVESIL 125 by MOMENTIVE, and in particular, a silicone cross-polymer sold by MOMENTIVE under the tradename VELVESIL FX having the following structure:

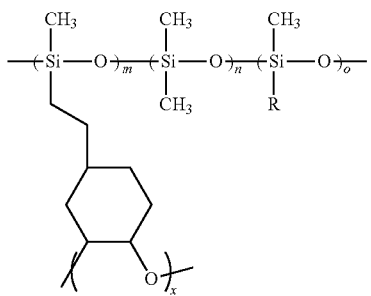

where R is, for example, a hydrocarbon radical, e.g., a $C_1$-$C_{20}$ hydrocarbon radical, x is typically from 2 to about 10, especially 2 to about 6, and most usually 2 to about 4, and m is generally from 1 to about 100, and n and o are generally from 0 to 100, with at least one of n or o being greater than zero. Elastomers such as VELVESIL DM and 034 generally are swelled in a silicone solvent (e.g., VELVESIL DM is about 18% by weight solids and 82% by weight dimethicone; VELVESIL 034 is about 16% by weight solids and about 84% caprylyl methicone) and typically have a viscosity of the swelled elastomer of from about 20,000 to about 2 million cps at 25° C., more typically from about 50,000 to about 1 million cps, and usually about 100,000 to about 750,000 cps. See Technical Brochure, MOMENTIVE PERFORMANCE MATERIALS, VELVESIL DM SILICONE (3/07); VELVESIL 034 organosilicone gel (3/10), each being incorporated herein by reference. VELVESIL FX is a gel-powder containing boron nitride particulates and having about 26% solids by weight. See Technical Brochure, MOMENTIVE VELVESIL FX GEL POWDER (3/08), incorporated by reference. The weight ratio of silicone elastomer gelling agent (e.g., dimethicone crosspolymer) to boron nitride for this type of elastomer may be, for example, 1:20 to 20:1, but will more commonly be from about 1:10 to about 10:1, and typically from about 1:5 to about 5:1. In some embodiments, the weight ratio of the boron nitride to the dimethicone crosspolymer will be about 3:1 to about 1:3, or about 2:1 to about 1:2, or about 3:2 to about 2:3.

The composition may also include additional colorants, such as pigments other than the first and second pigment components, lakes, dyes and particulate fillers. Any of the colorants mentioned above are useful for this purpose, including without limitation, iron oxides, red iron oxide, yellow iron oxide, black iron oxide, zinc oxide, titanium dioxide, talc, mica, sericite, calcium carbonate, magnesium silicate, aluminum magnesium silicate, silica, and pearls such as titanated mica, iron oxide titanated mica, bismuth oxychloride, and the like, and lakes of the FD&C and D&C dyes mentioned herein. Other suitable additional colorants include, for example, the pigments marketed as CHROMALITE which comprise colorants bonded to bismuth oxychloride with an alkali metal or alkaline earth metal (e.g., calcium) stearate.

The compositions may also include additional light diffusers, but are not limited to, nylon, polyurethane, silica beads, TOSPEARL (MOMENTIVE), poly (methyl methacrylate) (PMMA), polyethylene (PE), polystyrene (PS), polytetrafluoroethylene (PTFE, e.g., TEFLON), polymethylsiloxane, cellulose beads, boron nitride, mica, polyurethane powder, sericite, silica, fumed silica, fumed alumina, talc, titanium dioxide, zinc oxide, iron oxide, silicone powder and combinations thereof.

Suitable fillers include without limitation silica, treated silica, talc, zinc stearate, mica, kaolin, nylon particles or powders such as ORGASOL™, polyethylene particles or powder, TEFLON™, starch, boron nitride, copolymer microspheres such as EXPANCEL™ (NOBEL INDUSTRIES), POLYTRAP™ (DOW CORNING) and silicone resin microbeads (TOSPEARL™ from MOMENTIVE) or silicone elastomeric particles, and the like. Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, cellulose beads, ethylene glycol monostearate; inorganic white pigments such as magnesium oxide; and stabilizers/rheology modifiers, for example, BENTONE GEL and RHEOPEARL TT2. Other useful powders are disclosed in U.S. Pat. No. 5,688,831, the disclosure of which is hereby incorporated by reference.

The amount and type of the additional pigments and light diffusers used will vary depending upon the nature of the final product and the desired intensity of color; generally, however, the amount of such additional pigments will be about 1 wt % to about 75 wt %, and preferably about 5 wt % to about 50 wt %, by weight of the total composition, depending of course on the nature of the final cosmetic. In addition, microfine particulate pigments can be used at somewhat higher levels than those of normal particle size without significantly increasing the level of opacity of the composition on the skin can. Functional agents including without limitation, insect repellants, UV absorbers, UV blockers, antiperspirants, moisturizers, conditioners, tooth whiteners, and the like, may also be included.

These compositions are useful for foundations (e.g., liquid foundations, foundation mousses, foundation sticks, compact foundations, loose powders, compact powders, etc.), eye shadows, lipsticks, nail enamels, hair care products, skin care products, or personal care products, or the like.

The inventive pigment mixtures described herein provides improved optical blurring, soft focus, and high coverage. Thus, the compositions of the present invention may be free of, or substantially free of interference pigments, e.g., those based on mica and borosilicate, which are used primarily to provide a natural looking cosmetic film. Substantially free of interference pigments means less than about 5 percent, and preferably less than about 2 percent, and more preferred still less than about 1% by weight of the entire composition.

The cosmetic compositions will typically comprise a cosmetically acceptable vehicle. By "cosmetically acceptable" is meant that the vehicle is safe for contact with human skin and the like. It is contemplated that any cosmetically acceptable vehicle known in the art will be useful. The vehicle may comprise water, hydrophobic, and/or hydrophilic solvents. Suitable hydrophilic solvents include but are not limited to, butylene glycol, propylene glycol, pentylene glycol, caprylyl glycol, polyglycerol diisostearate, dimethylsiloxane/glycol copolymer, isopropyl myristate, triisostearyl citrate, or any combinations thereof. Suitable hydrophobic vehicles include hydrocarbon oils, which may be saturated or unsaturated, have an aliphatic character and be straight or branched chained or contain alicyclic or aromatic rings. Examples of preferred non-polar, volatile hydrocarbons include polydecanes such as isododecane and isodecane, including for example, PERMETHYL 99A (PRESPERSE INC.) and the $C_7$-$C_8$ through $C_{12}$-$C_{15}$ isoparaffins such as the ISOPAR SERIES available from EXXON CHEMICALS. A representative solvent is isododecane. Silicone oils are also contemplated to be suitable vehicles, including without limitation hexamethyldisiloxane (HMDS), polydimethylsiloxane (dimethicone) polymers, and cyclodimethicones. Suitable dimethicone polymers are available from DOW CORNING under the name DOW CORNING 200® Fluid and have viscosities ranging from 0.65 to 600,000 centistokes. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of cyclomethicones of varying viscosities include DOW CORNING 200, DOW CORNING 244, DOW CORNING 245, DOW CORNING 344, and DOW CORNING 345, (DOW CORNING CORP.); SF-1204 and SF-1202 SILICONE FLUIDS (MOMENTIVE), GE 7207 and 7158 (GENERAL ELECTRIC CO.); and SWS-03314 (SWS SILICONES CORP.). Polyethersiloxane copolymers are also contemplated as useful vehicles including, without limitation, polyoxyalkylene ether copolymers having a viscosity of about 1200 to 1500 centistokes at 25° C., including for example SF1066 organosilicone surfactant (MOMENTIVE).

A preferred vehicle component is dimethicone. Dimethicone may be used in combination with the gelling film formers described previously and in particular with a dimethicone cross-polymer film former. The composition may be in the form of an emulsion, including a water-in-oil, oil-in-water, silicone-in-water, or water-in-silicone emulsion, or the like. A suitable amount of emulsifier may be included to impart stability to the emulsion.

A composition as described herein may also comprise other components that may be chosen depending on the vehicle and/or the intended use of the composition. Additional components include, but are not limited to, water soluble sunscreens (such as EUSOLEX 232); oil soluble sunscreens (such as octyl methoxycinnamate); and other organic sunscreens (such as camphor derivatives, cinnamates, salicylates, benzophenones, triazines, PABA derivatives, diphenylacrylate derivatives, and dibenzoylmethane derivatives.); antioxidants (such as BHT); chelating agents (such as disodium EDTA); emulsion stabilizers (such as carbomer); preservatives (such as methyl paraben); fragrances (such as pinene); flavoring agents (such as sorbitol); humectants (such as glycerine); waterproofing agents (such as PVP/Eicosene copolymer); water soluble film-formers (such as hydroxypropyl methylcellulose); oil-soluble film formers (such as hydrogenated C-9 Resin); moisturizing agents, such as cholesterol; cationic polymers (such as Polyquaternium 10); anionic polymers (such as xanthan gum); pigment wetting agents, such as ARLACEL™. P100, or EMEREST™ 2452; vitamins (such as tocopherol); and the like.

The carrier (vehicle) will typically comprise from about 1% to about 99% by weight of the composition, and more typically between about 30% and about 80% by weight. In preferred embodiments, the carrier comprises between about 50% and about 70% by weight of the composition.

A composition comprising metal oxide particles of varying shapes and sized may be used in any type of hair treatment, skin treatment or makeup product. Such makeup products may include, but are not limited to, foundations, blushes, pressed or loose powders, concealers, bronzers, eyeshadows, eyeliners, lipsticks, and lipglosses. A composition as described herein may take any form which is typical of cosmetic products, for example, anhydrous compositions, aqueous systems, hot pour systems, water-in-oil emulsions, oil-in-water emulsions, water-in-silicone emulsions, silicone-in-water emulsions, gels, sticks, sprays, and pressed or loose powders. There is no limitation on the type of vehicle that may be employed. In particular, the identity of the vehicle will be largely controlled by the type of product into which the composition is to be incorporated. For a liquid foundation, for example, a water-in-oil emulsion may be used for aesthetic reasons, and although the oil portion of the vehicle may be any which is typically used for this purpose, it is preferred that the oil component comprise a silicone oil, either volatile or non-volatile. In one embodiment, a composition as described herein used in a liquid or powder foundation.

EXAMPLES

Example 1

A foundation having the formulation shown in Table 1 provide a natural look without sacrificing coverage.

TABLE 1

| Ingredient | Weight % |
|---|---|
| Isododecane | 5.25 |
| Acrylates Copolymer | 1.25 |
| Emollient | 15.2 |
| Emulsifiers | 3.0 |
| Cetearyl Dimethicone Crosspolymer/Boron Nitride Blend | 4.4 |
| Dimethicone | 8.8 |
| Zinc Oxide w/Dimethicone/Methicone Coating | 2.0 |
| Titanium Dioxide/Polymethyl Methacrylate Triethoxycaprylyl-silane Treated (Second Pigment—Atlas White/PMMA AS) | 2.0 |
| Calcium Carbonate (Cubic) | 2.5 |
| Alumina/Yellow Iron Oxides w/1% Triethoxycaprylyl-silane (First Pigment—COVALUMINE Sonoma Yellow AS) | 1.6 |
| Alumina/Black Iron Oxides/Silica Coated w/1% Triethoxy-caprylylsilane (First Pigment—COVALUMINE Sonoma Black) | 0.3 |
| Alumina/Red Iron Oxides, w/1% Triethoxycaprylylsilane (First Pigment—COVALUMINE Sonoma Red AS) | 0.5 |
| Alumina | 1.0 |
| Titanium .Dioxide w 1% Triethoxycaprylylsilane (Second Pigment) | 4.0 |
| Iron Oxide Yellow w/1%/Triethoxycaprylylsilane | 0.625 |
| Silica | 1.0 |
| Iron Oxide Red Pigment Grind | 0.4 |
| Iron Oxide Black Pigment Grind | 0.25 |
| Silica-Fumed | 0.5 |
| CHROMA-LITE Yellow-Methicone Coated | 0.75 |
| CHROMA-LITE Red-Methicone Coated | 0.35 |
| CHROMA-LITE Black-Methieone Coated | 0.15 |
| Nylon Powder | 1.5 |
| Polyurethane Crosspolymer | 1.5 |

TABLE 1-continued

| Ingredient | Weight % |
|---|---|
| Bismuth Oxychloride | 1.0 |
| Demineralized Water | qs |
| Butylene Glycol | 4.0 |
| Sodium Chloride | 1.5 |
| Preservatives | 0.8 |
| Fragrance | 0.05 |
| Liquid Foundation—Medium Beige | 100.0 |

Example 2

Sample Nos. 1-6 were prepared by admixing all of the ingredients under shear.

TABLE 2

| Ingredients | Sample No. | | | | | |
|---|---|---|---|---|---|---|
| | 1 | 2 | 3 | 4 | 5 | 6 |
| Cetearyl Dimethicone Crosspolymer/Boron Nitride Blend in Dimethicone (VELVESIL FX from MOMENTIVE PERFORMANCE MATERIALS) | | | | 47.5 | 47.5 | 47.5 |
| Alumina/Titanium Dioxide Coated w/1% Triethoxycaprylylsilane (First Pigment Component) (COVALUMINE ATLAS WHITE AS from SENSIENT COLORS INC.) | 5.0 | | 2.5 | 5.0 | | 2.5 |
| Titanium Dioxide Coated w/1% Triethoxycaprylylsilane (Second Pigment Component) (ATLAS WHITE AS from SENSIENT COLORS INC.) | | 5.0 | 2.5 | | 5.0 | 2.5 |
| Vinyl Dimethicone Crosspolymer/Cyclo-pentasiloxane/Dimethicone (SFE 839 from MOMENTIVE PERFORMANCE MATERIALS) | 47.5 | 47.5 | 47.5 | | | |
| Cyclomethicone Pentamer (SILICONE SF 1202 from MOMENTIVE PERFORMANCE MATERIALS) | 47.5 | 47.5 | 47.5 | 47.5 | 47.5 | 47.5 |
| Totals | 100 | 100 | 100 | 100 | 100 | 100 |

Figure 2:
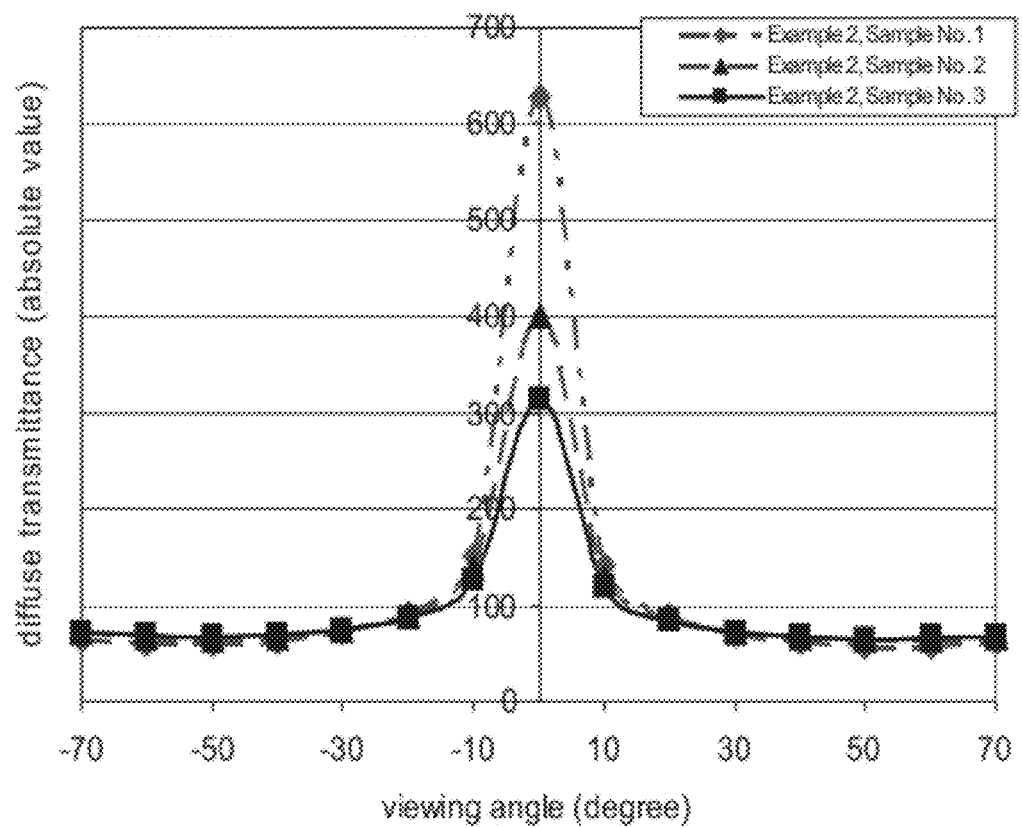
FIG. 2 is a graph of a viewing angle vs. diffuse transmittance for the Sample Nos. 1-3 in Example 2.
Figure 3:
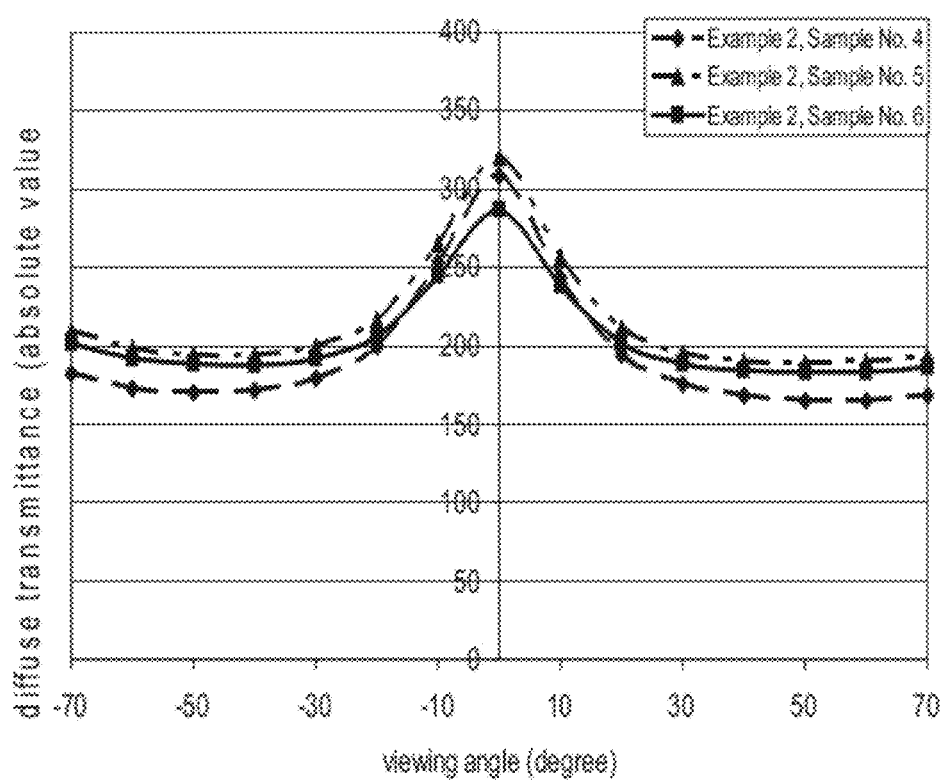
FIG. 3 is a graph of a viewing angle vs. diffuse transmittance for the Sample Nos. 4-6 in Example 2.

On a clean glass plate, the compositions were drawn down as a wet film of 3 mil thickness using a Gardner drawdown bar, and then allowed to dry at room temperature overnight. The next day measurements of the absolute unit of diffuse transmittance were measured as a function of viewing angle, with the results shown in FIGS. 2 and 3, where viewing angle is on the X-axis and diffuse transmittance is on the Y-axis. The multi-angle optical measurements are conducted on a GONIO SPECTROPHOTOMETER model GSP-1B, equipped with a GONIO SPECTROPHOTOMETCRI COLOR MEASURING SYSTEM model GCMS-3B from MURAKAMI COLOR LAB, Japan. During measurement, the glass plate bearing the samples is placed in vertical position. The light source is stationary and shines at 0 degree angle. The detector is mobile to collect measurements from various angles, from −70 to +70 degrees with step width of 10 degrees. The results show that the compositions of the invention comprising a 1:1 mixture of a first pigment that is a triethoxycaprylylsilane coated titanium dioxide on an alumina platelet substrate and a second pigment that is a spherical titanium dioxide in a medium containing a silicone crosspolymer (Samples Nos. 3 and 6) resulted in a reduction of the diffuse transmittance proximate to a viewing angle of zero degrees, and extending±10°. It is further seen that a viewing angle of ±10° from zero degrees presents the most challenge in terms of non-uniformity for applied make up, with reductions in this region providing a substantial benefit.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A cosmetic composition comprising: (i) a first pigment component comprising metal oxide particles bonded to an alumina platelet by an alkyl silane, (ii) a second pigment component comprising metal oxide particles, wherein said second pigment component comprises substantially spherical titanium dioxide particles whose surface is modified with alkylsilane groups, and (iii) a crosslinked silicone elastomer gelling agent.

2. The cosmetic composition of claim 1 further comprising calcium carbonate powder having a cubic crystalline form and an average particle size between about 0.1 and about 20 microns.

3. The cosmetic composition according to claim 1, wherein the weight ratio of said first pigment to said second pigment, is from about 1:5 to about 5:1.

4. The cosmetic composition according to claim 1, wherein the surface of said substantially spherical titanium dioxide particles is modified with triethoxycaprylylsilane.

5. The cosmetic composition according to claim 1, wherein the metal oxide particles are bonded to said alumina platelet with triethoxycaprylylsilane.

6. The cosmetic composition according to claim 1, wherein the weight ratio of said first pigment to said second pigment, is from about 1:2.5 to about 2.5:1.

7. The cosmetic composition according to claim 1, wherein said first pigment component comprises titanium dioxide particles bonded to an alumina platelet and said second pigment component comprises substantially spherical particles bonded to a substantially spherical polymethyl methacrylate substrate.

8. The cosmetic composition of claim 7 further comprising calcium carbonate powder having a cubic crystalline form and an average particle size between about 0.1 and about 20 microns.

9. The cosmetic composition according to claim 6, wherein the crosslinked silicone gelling agent comprises a particulate.

10. The cosmetic composition according to claim 9, wherein the particulate is boron nitride.

11. The cosmetic composition according to claim 10, wherein the crosslinked silicone gelling agent comprises a cyclic epoxide crosslinker.

12. The cosmetic composition according to claim 1, wherein the crosslinked silicone gelling agent has the structure:

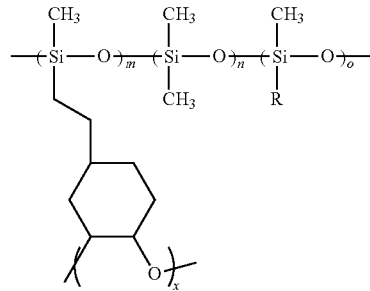

where R is a $C_1$-$C_{20}$ hydrocarbon radical, x is from 2 to 4, and m is generally from 1 to about 100, and n and o are generally from 0 to 100, with at least one of n or o being greater than zero.

13. The cosmetic composition according to claim 12, wherein the crosslinked silicone gelling agent comprises boron nitride.

14. The cosmetic composition of claim 1, further comprising one or more iron oxide pigments.

15. A cosmetic foundation comprising the cosmetic composition of claim 1.

16. A method of improving the uniformity of a cosmetic applied on a skin surface as viewed by an observer of the cosmetic on said skin surface at different angles, comprising topically applying to the skin surface a composition according to claim 1.

17. The method of claim 16, wherein the composition of claim 12 is applied to the skin.

* * * * *